United States Patent [19]

Greene et al.

[11] 4,147,171

[45] Apr. 3, 1979

[54] TRANSCUTANEOUS PAIN CONTROL AND/OR MUSCLE STIMULATING APPARATUS

[76] Inventors: Ronald W. Greene, 3116 S. 133rd St., Seattle, Wash. 98168; John L. Marshall, 16206-123rd Ave. SE., Renton, Wash. 98055

[21] Appl. No.: 763,542

[22] Filed: Jan. 28, 1977

[51] Int. Cl.² .................................................. A61N 1/36
[52] U.S. Cl. ....................................................... 128/421
[58] Field of Search .................... 128/419 R, 421, 422, 128/423 R

[56] References Cited

U.S. PATENT DOCUMENTS

| | | | |
|---|---|---|---|
| 2,771,554 | 11/1956 | Gratzl | 128/421 |
| 3,481,341 | 12/1969 | Siedband | 128/421 |
| 3,489,152 | 1/1970 | Barbara | 128/422 |
| 3,888,261 | 6/1975 | Maurer | 128/420 |
| 3,908,669 | 9/1975 | Man et al. | 128/422 |
| 3,911,930 | 10/1975 | Hagfors et al. | 128/421 |

OTHER PUBLICATIONS

Fridlund et al., "Behavior Research Methods & Instrumentation", vol. 8, No. 1, Feb., 1976, pp. 21–23.

*Primary Examiner*—William E. Kamm

[57] ABSTRACT

An apparatus for generating electrical pulses which are suitable for application to selected areas of the user's body for pain control or muscle stimulation. The current level, pulse width, pulse rate, voltage level and pulse configuration are all controlled to produce the desired effects. The apparatus includes a timing circuit which emits pulses of selected width and repetition rate. The pulses from the timing circuit energize a switching circuit which selectively connects the primary of a pulse transformer to a power source. The transformer is so constructed and arranged that it operates near saturation, thereby effectively operating as a current limiter, which helps to prevent spikes in the electrical pulse output of the apparatus.

8 Claims, 4 Drawing Figures

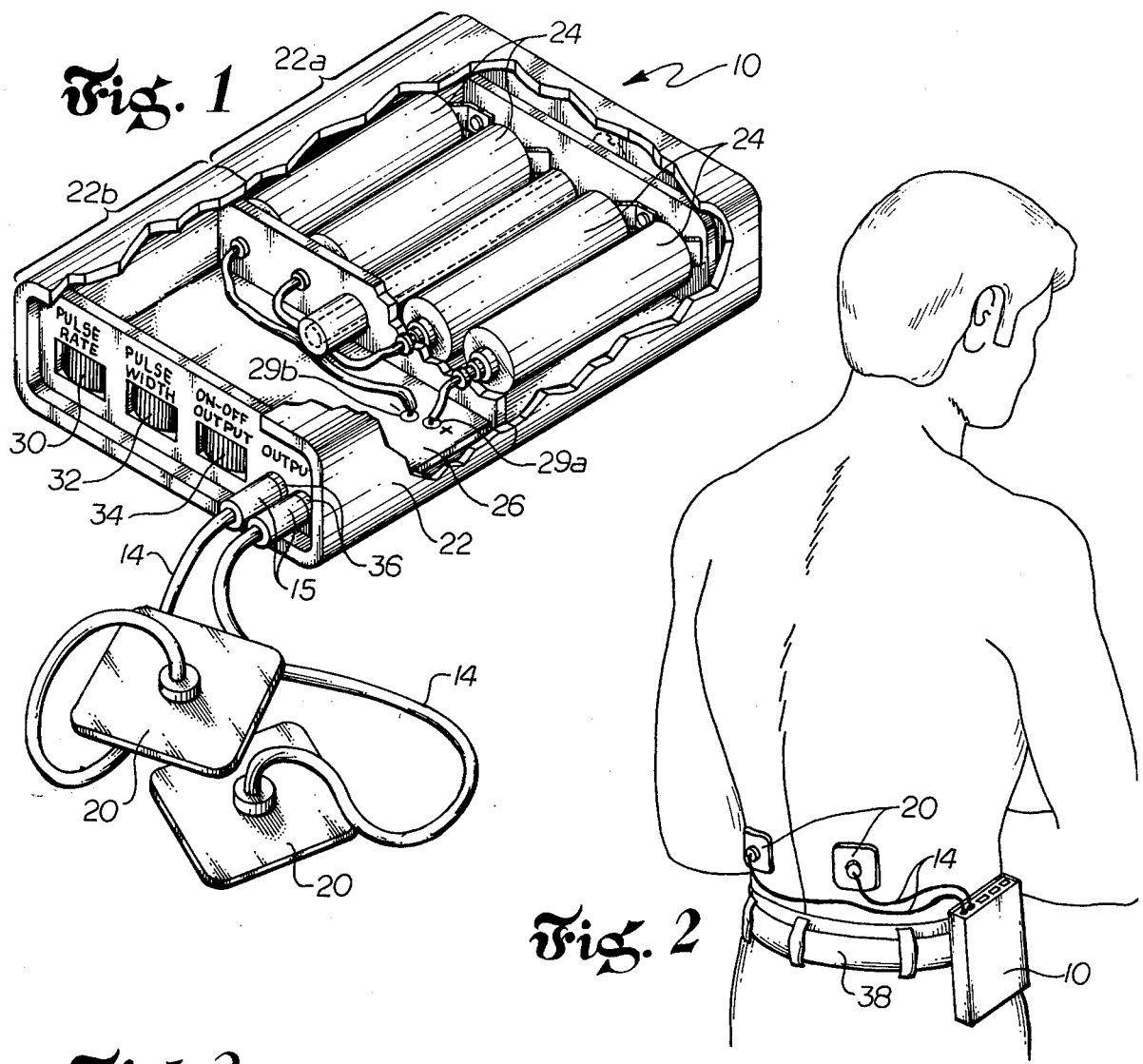
Fig. 1
Fig. 2
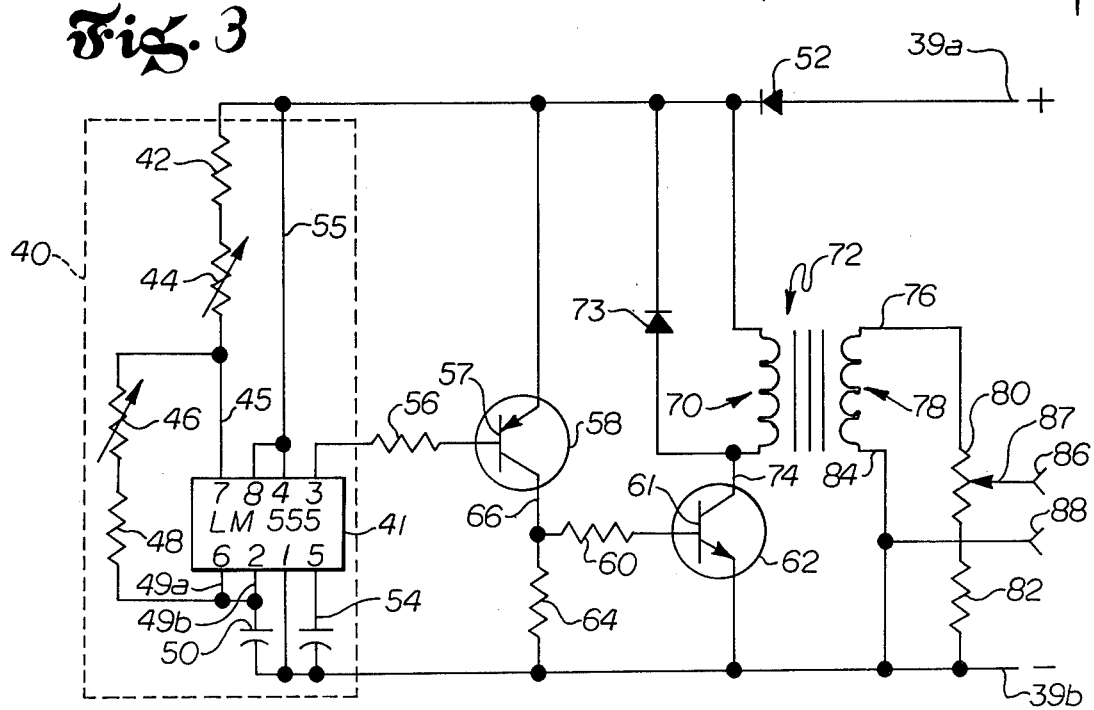
Fig. 3

TRANSCUTANEOUS PAIN CONTROL AND/OR MUSCLE STIMULATING APPARATUS

BACKGROUND OF THE INVENTION

The general effect of externally-applied electrical energy on the operation of the central nervous system, particularly for control of pain, has been observed since the early 1900's. The use of electrical energy as a predictable, reliable treatment for control and/or elimination of pain, however, has not heretofore been very successful. In general, the technology in this art area has remained relatively static for a considerable period of time.

The lack of success with electrical pain control devices is due to a large extent to the imperfect understanding of how the phenomenon of pain is produced, transmitted and finally recognized by the brain. There are several current theories on pain, the most recent and perhaps most widely accepted of which is the gate control theory, as described in the article by Melzack and Wall entitled "Pain Mechanisms, A New Theory;" appearing in Science vol. 150 at p. 971 (1965). This theory, in its simplest form, proposes the existence of a particular type of cell, referred to as "substantia gelatanosa", or simply, T-cells, which are located between the large and/or small nerve fibers and the biologic system which transmits any nerve stimulus to the brain.

Under the gate control theory, the pain stimulus is transmitted to the T-cells and eventually to the brain in the form of electrical pulses. Extraneous electrical pulses, such as those produced by a pain control device, when directed through the T-cells into the large nerve fibers, exert an inhibiting or blocking effect on the transmission of pain impulses to the brain from both the small and large nerve fibers, hence reducing or eliminating the recognition and subsequent experience of pain.

According to this theory, the extraneous electrical pulses must be accurately delivered to specific nerve endings, and it has been found experimentally that careful, precise location of the electrodes of a pain control device has improved their performance.

Nevertheless, the gate control theory does not account for all of the phenomena in the experience of pain, and the precise physical manner in which pain impulses are recognized and transmitted by the human body is still imperfectly understood. Further, the amount of relief provided by prior art electrical pain control devices varies significantly, largely for unknown reasons. It is not currently understood why some patients respond favorably to pain control devices and others do not. Hence, progress in the design of electrical pain control devices is still often obtained through intuition, experimentation, and generally empirical methodology.

Furthermore, at the time of the present invention, there were relatively few guidelines concerning the correct pulse configuration, pulse deviation and pulse rate, primarily because of the lack of theoretical understanding of the pain phenomenon.

Additionally, prior art devices have been found to be susceptible to the presence of large spikes in the pulses applied to the user's body, caused either by very low skin resistance or the inherent operation of the electrical circuit generating the pulses. The possibility of such current spikes, particularly at the rise and fall of the pulses, has prevented wide use and/or acceptance of such devices because of the health hazard involved.

The present inventors, however, after reviewing the experimental results obtained by many prior art devices and after a substantial amount of their own experimentation, have established operating parameters for the pulsed output of a pain control device which has provided substantially improved results. The inventors have designed and built a circuit which is capable of meeting the established parameters, and which eliminates, in a relatively inexpensive manner, the possibility of spikes in the output of the device. This circuit, which is described in detail hereinafter, was developed in accordance with the following objects.

It is a general object of the present invention to provide an electrical pain control and/or muscle stimulating device which overcomes one or more of the disadvantages of the prior art noted above.

It is another object of the present invention to provide such a device which eliminates or reduces pain in affected areas of the body for a substantial percentage of users.

It is a further object of the present invention to provide such a device which is not harmful to the user.

It is an additional object of the present invention to provide such a device which may be conveniently carried on the person of the user.

It is a still further object of the present invention to provide such a circuit which operates for extended periods of time without the necessity of battery recharge or replacement.

It is yet another object of the present invention to provide such a device which can be used for different types of pain.

It is an additional object of the present invention to provide such a circuit which eliminates the possibility of spikes in the pulse output of the apparatus.

It is a further object of the present invention to provide such a device which produces maximum reduction of pain with minimum discomfort to the user.

It is a still further object of the present invention to provide such a device which takes advantage of the actual operation of the pain stimulus and transmission system of the human body.

It is an additional object of the present invention to provide such a device which can be conveniently used to retain damaged muscles.

It is an additional object of the present invention to provide such a device which can be controlled remotely.

SUMMARY OF THE INVENTION

Accordingly, an apparatus is provided for generating a series of electrical impulses which are particularly suitable for application to selected areas of the human body to reduce pain and/or to stimulate muscles. The apparatus includes a circuit for generating control pulses, a transformer having particular operating characteristics, a switching device controlled by the control pulses for energizing the transformer, and a load circuit which develops the electrical impulses for application to the user's body at the secondary of the transformer. The control pulses are of selected rate and duration, while the switching device is operative to connect the primary winding of the transformer to a source of supply voltage for the duration of each control pulse. The characteristics of the transformer are important, since the transformer, which has primary and secondary windings, is so constructed and arranged that it operates near a saturation level when the current of the electrical impulses developed at the secondary winding is at a pre-selected level which is safe for use on human beings. Operating the transformer at near saturation helps to prevent current spikes in the electrical impulses developed at the secondary of the transformer, which are in turn applied to the user's body.

DETAILED DESCRIPTION OF DRAWINGS

A more thorough understanding of the invention may be obtained by a study of the following detailed description taken in connection with the accompanying drawings in which:

FIG. 1 is an isometric, partially cutaway, view showing the general configuration of the pain control device of the present invention, in combination with additional apparatus for applying the pulses generated by the device to the body of a user.

FIG. 2 is a schematic view of the pain control device of FIG. 1 showing a typical operative placement of the device on the body of a human user.

FIG. 3 is a schematic diagram of a first embodiment of the electrical circuit used in the pain control device of FIG. 1.

DESCRIPTION OF PREFERRED EMBODIMENT

Figure 4:
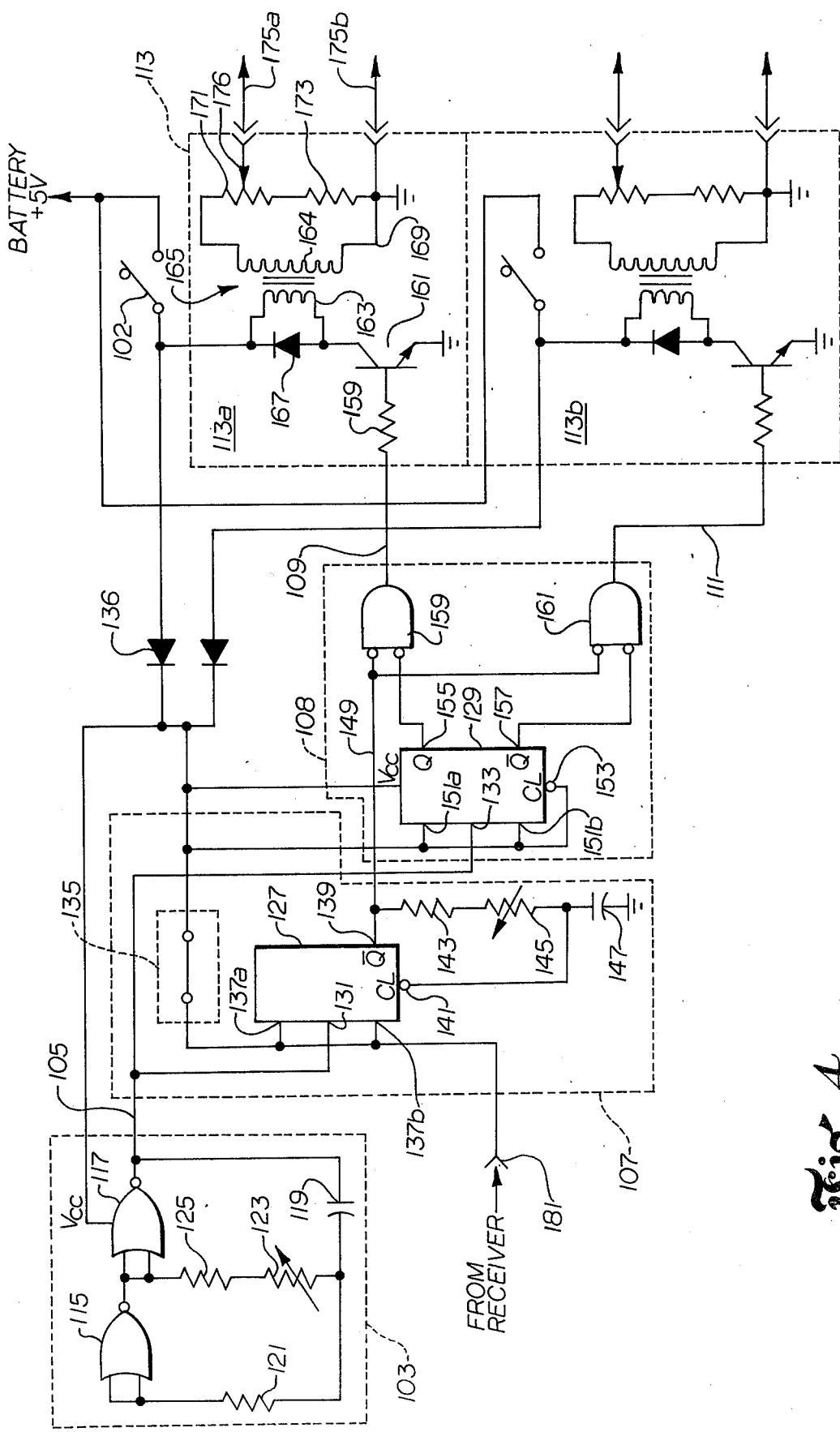
FIG. 4 is a schematic diagram of a second embodiment of the electrical circuit used in the pain control device of FIG. 1.

Prior to the actual design of the electrical circuit which is used in the present invention to generate the electrical pulses which are applied to the pain-affected areas of the body, the present inventors established several criteria for the configuration of the electrical pulses and operation of the electrical circuit. The device developed by the inventors implementing these criteria has in actual practice provided significantly improved and more uniform results over prior art pain control devices.

These criteria included the following: (1) the voltage level of the electrical pulses must be as low as possible, minimizing battery requirements, and avoiding injury via burning, especially in those tissues immediately surrounding the nerve endings to be stimulated; (2) a sufficient amount of energy per given unit of time must be supplied to the nerve endings to produce desired results; (3) the electrical pulses delivered into the pain-affected area should be current-limited, i.e. very low skin resistance should not result in an increase in current above a pre-selected known safe level; and (4) the configuration of the electrical pulses must be as pure as possible, i.e. there must be no ringing on either the rise or fall of the individual electrical pulses.

The particular output pulse best meeting the above design criteria was recognized by the present inventors to be a pure rectangular wave. The rectangular pulses produced by the circuit of the present invention have several desirable characteristics and in the accomplishment of the objectives of the invention. Each pulse is relatively pure i.e. it is free from ringing or other distortion. Further, the configuration of the pulse remains constant over a wide variation of load impedance, as the impedance of human skin ranges from virtually zero to as high as 50K ohms.

The circuit was designed to be current-limited, and to operate at current levels near the selected limit, so that current spikes are eliminated from the pulse output. Furthermore, the circuit was designed to permit control over the width and repetition rate of the pulses.

Such a circuit, adapted for pain control and/or muscle stimulating applications, combines various structural features in a manner not heretofore appreciated or recognized by the prior art. The combination herein disclosed and claimed has been shown in actual practice to produce significantly improved results over prior art devices.

FIG. 1 shows an isometric, partially cutaway, view of the complete pain control device of the present invention, in a form which is ready for use with human beings. The pain control device is shown generally at 10, in combination with electrical leads 14—14 and electrodes 20—20. At one end of each electrical lead 14—14 is attached a probe 15 for electrical connection with pain control device 10, and at the other end is attached an electrode 20, which is adapted to be secured to the body in the vicinity of the pain-affected portion thereof.

Device 10 includes a case 22 of conventional design. Case 22 is divided into two portions, one portion being a power module 22a containing batteries 24—24 which supply the power for device 10 and the other portion being a control module 22b containing: (1) an electronic circuit 26 which generates the output pulses, (2) a set of controls 30, 32, 34 for electronic circuit 26, and (3) two output jacks 36—36.

In the preferred embodiment, case 22 is adapted to permit convenient access, by means of a cover or the like (not shown), to batteries 24—24, which are held in position in power module 22a by conventional securing means (not shown). The combined electrical output of the batteries, which in the preferred embodiment is five volts produced by four nickel-cadmium AA batteries, is applied to control module 22b through power inputs 29a and 29b, and specifically to electronic circuit 26. Electronic circuit 26, energized by the current supplied by batteries 24—24, produces in operation the electrical output pulses which are then applied through output jacks 36—36, electrical leads 14—14 and electrodes 20—20 to the pain-affected area of the body. Electrodes 20—20 may be of various configuration and/or sizes, and are typically secured to the user's body by a suitable adhesive.

The configuration of the output pulses produced by electronic circuit 26 is controlled by pulse rate control 30, pulse width control 32, and an on-off switch/output level control 34. Each control 30, 32 and 34 includes, in the preferred embodiment, knurled rotatable discs, movement of which alters the value of the appropriate variable resistances (not shown) in electronic circuit 26.

Case 22 is sufficiently compact and lightweight that it may be conveniently carried on the person of a user. The case shown and described herein is 4.6 inches long, 3.2 inches wide, 1.1 inches high, and weighs approximately 12 ounces. Case 22 also includes a conventional snap holder (not shown), which is used to secure device 10 to the user's clothing or other support means. In FIG. 2, device 10 is shown secured to a user's belt 38.

FIG. 3 shows the schematic for a first embodiment of electronic circuit 25, as energized by a five (5) volt power supply through plus and minus terminals 39a, 39b. Five volts is the minimum voltage necessary to operate timing circuit 40, which includes charging and discharging circuits and an integrated circuit 41 known commercially as an LM 555 or equivalent.

Basically, LM 555 comprises a trigger circuit and a conventional bistable multi-vibrator (flip-flop). The trigger circuit includes two comparators which are responsive to the supply voltage and the voltage present at certain input pin connections to the LM 555. In operation, the flip-flop changes state under the control of the comparators at input voltage levels corresponding to one-third and two-thirds of the supply voltage level. The output of LM 555 at pin 3, which is the output of timing circuit 40, is hence a series of pulses, the relative pulse duration and pulse interval of which are established by the values of the elements comprising the charging and discharging circuits of timing circuit 40.

The charging circuit portion of timing circuit 40 comprises a series connection of a first fixed resistance 42, a first variable resistance 44, a second variable resistance 46, a second fixed resistance 48, and a capacitor 50. The charging circuit is thus in effect connected in series between plus and minus terminals 39a and 39b. A wire connection 45 is provided from a point intermediate of variable resistances 44 and 46 to pin 7 of the LM 555, while other wire connections 49a and 49b are provided from a point intermediate of fixed resistance 48 and capacitor 50 to pins 6 and 2, respectively, of the LM 555.

In the operation of timing circuit 40, current proceeds from plus terminal 39a through diode 52, which is connected so as to prevent current flow when the polarity of the battery is reversed, and then through the charging circuit comprising the series connection of fixed and variable resistances 42, 44, 46 and 48, eventually charging capacitor 50. Battery voltage is also provided through wire connection 55 to pin 8 of the LM 555, which is a Vcc connection, and pin 4 thereof, which is a reset-disable connection.

The voltage on capacitor 50 will increase until it reaches a level which is two-thirds that of the supply voltage. At that point, the flip-flop in the LM 555 will change state, under the control of one of the comparators, and as a result of additional internal connections, pin 7 of the LM 555 will go to ground, thus providing a discharge path to ground for capacitor 50 through fixed resistance 48 and variable resistance 46. Capacitor 50 continues to discharge until its voltage level reaches a value which is one-third that of the supply voltage, at which point the LM 555 flip-flop changes state again, which results in pin 7 of the LM 555 being reset to its floating state. Capacitor 50 then again begins to charge toward the value of the supply voltage.

The output of the LM 555 at pin 3 will be at +5 volts until the voltage on capacitor 50 reaches a level which is two-thirds that of the supply voltage, at which point the output voltage drops to zero volts. As long as capacitor 50 continues to discharge, the voltage at pin 3 of the LM 555 is zero volts. When the voltage on capacitor 50 decreases to one-third of the supply voltage, the voltage at pin 3 rises again to +5 volts. The duration of the resulting negative-going pulse is controlled by the values of variable resistance 46 and fixed resistance 48.

In the preferred embodiment, fixed resistance 48 establishes the minimum pulse width and is 1.1 Kohms, while variable resistance 48 is 0-5 Kohms. The time constant of the discharging circuit is very fast compared to the time constant of the charging circuit, as will be clarified hereinafter. The above values of resistance result in a pulse duration variable between 80 and 500 microseconds. This range has been found by the inventors to provide good results. Changes in the range boundaries, however, may be accomplished by varying the values of resistances 46 and 48.

The total value of resistance in the charging circuit controls the value of the pulse repetition rate, and hence to an extent the interval between successive pulses, since the charging circuit is dominated by the values of resistances 42 and 44 because they are substantially larger than the values of resistances 46 and 48. Fixed resistance 42, which establishes a minimum pulse rate, is 75 Kohms in the preferred embodiment, while variable resistance 44 is variable between 0 and 1 megohm. This combination provides a pulse rate variable between 15 and 115 pulses per second. Again, this range has been found by the inventors to be particularly effective on actual patients.

Capacitor 54 is connected between unused pin 5 of the LM 555 and minus terminal 39b solely for purposes of stabilizing the supply voltage reference for the two-thirds comparator, and is hence of no substantial significance to the operation of timing circuit 40.

As stated above, the output from timing circuit 40 is in the form of negative-going pulses, which are then applied through resistance 56 through to the base 57 of a transistor 58, turning it on. Resistance 56 is 10 Kohms in the embodiment shown, sufficiently small in value to insure saturation of transistor 58 when it is on.

When transistor 58 turns on, a current path is provided from the plus terminal 39a through the emitter-collector path of transistor 58 and resistance 60 to the base 61 of transistor 62, which preferably is a Darlinton-connected transistor. The value of resistance 60 is selected to limit the current flow into transistor 62. In the embodiment shown, resistance 60 is 390 ohms.

Resistance 64 is connected between collector 66 of transistor 58 and minus terminal 39b, and is of sufficient value, on the order of 10 Kohms, to prevent turn-on of transistor 62 from the leakage current through transistor 62 when transistor 58 is off.

When transistor 62 turns on, current flows from plus terminal 39a down through primary winding 70 of a transformer 72, through the collector-emitter circuit of transistor 62, to minus terminal 39b. A diode 73 is connected between collector 74 of transistor 62 and the top of primary winding 70, and in operation provides a path for the flow of reverse current caused by the collapse of the magnetic field around primary winding 70, and thereby clamps the reverse primary voltage generated in the normal action of transformer 72. Diode 73 thus prevents large negative spikes in the electrical impulses provided at the circuit output, eliminating one possible source of skin burns.

Further, transformer 72 is selected so that it operates near saturation when the output current level is 20-22 Ma. Transformer 72 thus acts as a current-limiter, and prevents large positive current spikes since it operates near saturation. This is a convenient and inexpensive solution to the serious problem of spikes in the output signal.

Upper end 76 of secondary winding 78 is connected through a variable resistance 80 and a fixed resistance 82 to the minus terminal 39b, while lower end 84 of secondary winding 78 is connected directly to the minus terminal 39b. One output connection 86 which is electrically connected to one output jack 36 (FIG. 1) is connected to the movable arm 87 of variable resistance 80, while the other output connection 88, which is electrically connected to the other output jack 36 is connected directly to lower end 84 for secondary winding 78.

In the embodiment shown and described, the combination of fixed resistance 82, which is 5 Kohms and variable resistance 80, which is variable between 0 and 5 Kohms, results in an output voltage range of 60 to 120 volts, with constant output current adjustable from 0–20 Ma into a load impedance of zero to 4,000 ohms. The output voltage range may be varied by changing the values of resistances 80 and 82 and/or the turns ratio of transformer 72.

In operation, device 10 is positioned so as to be supported on the person of the user in proximity to the pain-affected area of the body. Electrodes 20—20 are then positioned over the proper nerves and secured to the body. After the device 10 is turned on, the voltage level of the output is gradually increased from a minimum, at a minimum pulse repetition rate, by means of control 34, i.e. by variation of variable resistance 80 through its associated knurled control knob, until a physical perception of the electrical pulses is experienced by the user.

The pulse repetition rate is then varied by means of control 30 until the pain experienced by the user is minimized. The pulse width is then varied by control 32 and the pulse level decreased by control 34 until the precise point is reached when the pain is either minimized or entirely eliminated, and the pulse level is at a minimum. Continuous pain relief is provided at this setting with minimum risk or discomfort to the user.

Referring now to FIG. 4, another embodiment of electronic circuit 26 is shown which is particularly useful in a dual probe pain control device used in special purpose applications, such as for lower back pain. Alternatively, the embodiment of FIG. 4 is useful, with some modification in the element values and in combination with a remote gating circuit, to stimulate muscles, for the retraining of paralytics or others similarly situated.

The circuit shown in schematic form in FIG. 4 shares many design similarities with the circuit of FIG. 3, especially in the output section. The circuit of FIG. 4 is divided into four basic sections, by function. The first section 103 is an oscillator, and generates a square wave of controlled width and amplitude on line 105 for use by the remainder of the circuit. In the embodiment shown, the frequency of the square wave output of oscillator section 103 varies between 5.7 Hz and 260 Hz, as determined by the value of variable resistance 123.

Oscillator section 103 drives a monostable multivibrator (one-shot) section 107, which is responsive to the square wave signal on line 105 to produce a series of pulses on line 149. The pulses on line 149 are variable in width between 70 microseconds to 350 microseconds in the embodiment shown, as determined by the value of variable resistance 145.

A bistable multivibrator (flip-flop) section 108 receives the pulses on line 149 from one-shot section 107 and produces alternating control pulses on lines 109 and 111. An output section 113 is responsive to the control pulses on lines 109 and 111, respectively, to provide pulse output signals from two identical portions 113a, 113b of output section 113. The pulse output signals are suitable for direct application to the affected areas of the body, through electrical leads and electrodes similar to those described above.

Referring now to oscillator section 103 in detail, two two-input NOR gates 115 and 117 are connected in series, and receive Vcc power through diode 136 and switch 102 from the battery. NOR gates 115 and 117 form one-half of a four NOR gate integrated circuit chip known commercially under the number 74C02, or equivalent. The output of NOR gate 117 is connected to the input of NOR gate 115 through a series connection of capacitor 119 and fixed resistance 121, and is further connected to its own input through a series circuit of capacitor 119, variable resistance 123 and fixed resistance 125.

In operation, oscillator section 103 generates a square wave as follows: assume that the input to NOR gate 115 is high, with its output and hence the input to NOR gate 117 being both low. The output of NOR gate 117 is hence high. Previously, capacitor 119 has been charged when the output of NOR gate 117 was low. Capacitor 119 begins to discharge through resistances 123 and 125 when the output of NOR gate 117 goes high, with NOR gate 115 sinking, or carrying, the discharge current. Resistance 121 samples the discharge current, and when the voltage present at the input of NOR gate 115 decreases below its threshold voltage, its output is again forced high, which forces the input of NOR gate 117 high.

When the input of NOR gate 117 goes high, its output is forced low, and capacitor 119 begins to charge. Capacitor 119 continues to charge until its voltage is sufficiently high that the voltage at the input of NOR gate 115 rises above its threshold voltage, at which point the output of NOR gate 115 and the input of NOR gate 117 again both go low, forcing the output of NOR gate 117 to again go high. Oscillations in the form of a square wave at the output of NOR gate 117 on line 105 are thus sustained.

The amplitude and timing of the transistors of the square-wave output from oscillator section 103 is controlled by the value of the capacitive and resistive elements in the circuit, particularly the value of variable resistance 123. In the embodiment shown and described, fixed resistance 121 is 2.2 megohms, fixed resistance 125 is 100 Kohms, variable resistance 123 is a potentiometer variable between 0 and 1 megohm, and capacitor 119 is 0.015 microfarads. This results in a square wave output having a frequency range between 5.7 Hz and 260 Hz.

The signal on line 105 from oscillator section 103 is applied to a clock input 131 of a first J-K flip-flop circuit 127. J-K flip-flop circuit 127 is connected in FIG. 4 as a monostable multivibrator (one-shot). Vcc is connected through a conducting connection 135 to J & K terminals 137a and 137b of circuit 127. Conducting connection 135 is typically a portion of a copper land on the printed circuit board which is convenient to cut. Also connected to J & K terminals 137a and 137b is a line adapted to be connected to a remote receiver (not shown) which in operation keys, or operates, the device remotely, as will be explained in following paragraphs.

Circuit 127 has a $\bar{Q}$ output terminal 139 and a negative clear terminal 141. Connected in series between $\bar{Q}$ terminal 139 and ground is fixed resistance 143, variable resistance 145 and capacitor 147. A line connection exists between negative clear terminal 141 and a point intermediate of capacitor 147 and variable resistance 145.

In operation, a voltage is present at $\bar{Q}$ terminal 139 when circuit 127 is in its stable state, maintaining capacitor 147 charged through resistances 143 and 145. When the voltage at $\bar{Q}$ terminal 139 goes low, due to a pulse from oscillator section 103 at clock input 131, capacitor 147 discharges into $\bar{Q}$ terminal 139 through resistances 143 and 145. The discharge of capacitor 147 continues until its voltage level is below the threshold voltage of negative clear terminal 141, at which point circuit 127 is cleared and returned to its stable state, with the voltage at $\bar{Q}$ terminal 139 again high.

The output at $\bar{Q}$ terminal is thus a negative-going pulse series, the pulse duration of which is controlled by the value of resistances 145 and 143. In the present embodiment shown and described, fixed resistance 143 is 1.1 Kohms, variable resistance 145 is a 5 Kohm potentiometer, and capacitor 147 is 0.068 microfarads. This results in a negative-going pulse series having a pulse width variable between 70 and 350 microseconds.

The output of oscillator section 103 is also applied to a clock input 133 of J-K flip-flop 129, which is connected as a bistable multivibrator (flip-flop). J-K flip-flop circuits 127 and 129 are provided in the embodiment shown on a single dual J-K flip-flop integrated circuit chip known commercially under the number 74C107, or equivalent.

In circuit 129, Vcc power is provided through switch 102 and diode 136 to J & K terminals 151a and 151b, as well as to negative clear terminal 153. Circuit 129 has both a Q output terminal 155 and a $\bar{Q}$ output terminal 157. Output terminals 155 and 157, respectively, are connected to one input of two two-input negative AND gates 159 and 161. Negative AND gates 159 and 161 comprise the other half of the four NOR gate chip with NOR gates 115 and 117. The other input to negative AND gates 159 and 161 is supplied by the $\bar{Q}$ output from circuit 127 on signal line 149. The output of negative AND gate 159 is provided on line 109, while the output of negative AND gate 161 is supplied on line 111. The signals on lines 109 and 111 are, respectively, the control pulses which are applied to the two portions 113a, 113b of output section 113.

In operation, J and K terminals 151a and 151b and negative clear terminal 153, being all tied to Vcc, are maintained high. Circuit 129 operates essentially as a divide-by-2 multivibrator with the signal output at the Q and $\bar{Q}$ terminals 155 and 157, respectively, going alternately high and low in response to the square wave input from oscillator section 103 at clock input 133. Thus, when the voltage at output terminal 155 is high, the voltage at output terminal 157 is low and vice versa. The signal at each output terminal thus is a series of pulses, at one-half the frequency of the square wave from oscillator section 103.

The output of each negative AND gate 159 and 161 will be high only when its respective two inputs are concurrently low. Thus the output of negative AND gate 159 will be high only when the voltage at Q output terminal 155 is low concurrently in time with the negative-going pulse from circuit 127 on line 149. Likewise, the output of negative AND gate 161 will be high only when the voltage at $\bar{Q}$ output terminal 157 is low concurrently in time with the negative going pulse from circuit 127 on line 149.

The control pulses from negative AND gates 159 and 161 on lines 109 and 111 are then applied, respectively, to identical portions 113a and 113b of output section 113. Output section 113 is very similar to the corresponding portion of the circuit embodiment of FIG. 3 and provides the same advantages in preventing current spikes in the output. Referring to the structure and operation of portion 113a as an example, a control pulse on line 109 is applied through a resistance 159 to the base of a transistor 161, which has its collector-emitter circuit connected in series between primary winding 163 of a transformer 165 and ground. Primary winding 163 is shunted by a diode 167 to provide a path for the reverse current caused by the collapse of the magnetic field around primary winding 163 during each oscillation of the control signal on line 109.

Secondary winding 164 of transformer 165 is shunted by a series connection of fixed resistance 173 and variable resistance 171. The lower end 169 of secondary winding 164 is connected to ground. An output connection 175a which is electrically connected to one output jack in the first pair thereof is connected to the movable arm 176 of variable resistance 171, while output connection 175b which is electrically connected to the other output jack in the first pair is connected to the lower end 169 of secondary winding 164.

Output section 113 is very similar in structure and operation to the output section of the embodiment shown in FIG. 3. Transformer 165 operates near saturation, which aids significantly in maintaining the desired purity of the square wave configuration, and assists in eliminating current spikes from the output pulses.

The apparatus shown in FIG. 4 may be conveniently used as a dual probe pain control device, and is particularly useful for certain types of lower back pain for which two pulse series are necessary.

The inventors have found for the embodiment of FIG. 4 that when each control is set near the high end of its range, and the electrodes positioned over muscles, the resulting pulse output will produce a muscle stimulus and will result in a contraction of the muscle. A pulse rate of approximately 150 pps, with pulse width and pulse level in the upper third of their respective ranges, has provided good results. Operating in such a mode, the device is useful both in facilitating exercise of bedridden patients and in retraining paralytics or others similarly situated.

When the device of FIG. 4 is used for muscle retraining, it should be remotely keyed. This capability is provided in the embodiment of FIG. 4 through the use of a remote keying receiver (not shown) which connects into the circuit through remote terminal 181.

In the remote keying mode, conductive connection 135 is cut, and input power is provided to the circuit not from the battery through switch 102, but selectively by operation of the keying receiver by an operator.

Although the present invention has been described in terms of transcutaneous application of electrical pulse energy, meaning that the electrical energy is applied to the surface of the skin of the user through electrodes or like means, it should also be understood that the same circuit principles disclosed herein are applicable to subcutaneous pulse energy application.

Thus, an apparatus is disclosed which generates pulse energy for application to selected areas of the body. The circuit is designed so as to provide output pulses in the form of pure rectangular waves, having a constant current output over a certain load range and without the danger of current spikes. The voltage level, pulse rate, and pulse width are all selectively controllable over defined ranges. Such a device has been found to provide better and more uniform results than heretofore achieved by the prior art.

It should be understood, however, that various changes, modifications and substitutions may be made in the disclosed apparatus by a man skilled in the art without departing from the spirit of the invention, which is defined by the claims which follow.

What is claimed is:

1. An apparatus for treating pain and for stimulation of muscles in the human body by electrical impulses, comprising:

means for generating control pulses of selected rate and duration, wherein said generating means includes (1) timing means, having a trigger input connection, providing in operation an output signal with first and second stable states, the output signal changing from said first stable state to said second stable state when the voltage at said trigger input rises to a first fraction of the supply voltage and further changing from said second stable state to said first stable state when the voltage at the trigger input decreases to a second fraction of the supply voltage, (2) a charging circuit which is initially connected between the supply voltage and said trigger input when the voltage at said trigger input decreases to said second fraction of the supply voltage, and which remains so connected as long as the voltage at the trigger input is increasing but below said first fraction of the supply voltage, (3) a discharging circuit which is initially connected between said trigger input and ground when said voltage at said trigger input reaches said first fraction of the supply voltage, and which remains so connected as long as said voltage at said trigger input is decreasing but above said second fraction of the supply voltage; and transformer means having primary and secondary windings for producing, under the control of said control pulses, by transformer action, electrical impulses at the secondary of said transformer means of desired rate, duration, and amplitude for application to the human body, wherein the operating characteristics of the transformer are such that the transformer operates near, but not in, saturation over the range of effective current output of the apparatus.

2. An apparatus of 1, including a diode connected across the primary winding of said transformer means, the anode of said diode being common to the lower end of the primary winding.

3. An apparatus of claim 1, including a source of supply voltage, and switching means responsive to said pulses for selectively connecting the primary winding of said transformer means to said source of supply voltage for the duration of each control pulse.

4. An apparatus of claim 3, wherein said source of supply voltage includes positive and negative terminals, and wherein said charging circuit includes (1) a series connection of a resistance means and a first capacitor, (2) means connecting one end of said resistance means to the positive terminal of the supply voltage, (3) means connecting the other end of said resistance means to said trigger input, (4) means connecting one end of said first capacitor to said trigger input, and (5) means connecting the other end of said first capacitor to the negative terminal of the supply voltage.

5. An apparatus of claim 4, wherein said resistance means has first and second resistance sections and a circuit connection point therebetween, and wherein said discharging means includes means selectively connecting said circuit connection point to ground.

6. An apparatus of claim 5, wherein each of said first and second resistance sections includes a series connection of a fixed resistance and a variable resistance, said first resistance section being connected between the positive terminal of the source of supply voltage and the circuit connection point, wherein the value of resistance present in said first resistance section determines the pulse rate of the control pulses, and wherein the total value of resistance present in said first and second resistance sections determines the pulse width of the control pulses.

7. An apparatus of claim 3, wherein the electrical impulses comprise a relatively pure square wave, regardless of the load placed on the apparatus by the human body to which the impulses are applied.

8. An apparatus of claim 7, wherein the rate of the control pulses is within the range of 15 to 115 pulses per second, and wherein the duration of said control pulses is within the range of 80 to 500 microseconds.

* * * * *